United States Patent
Hudon et al.

(10) Patent No.: US 8,449,459 B2
(45) Date of Patent: May 28, 2013

(54) ACCESS PORTAL INCLUDING SILICONE FOAM THREE LAYER SEAL

(75) Inventors: Andrew Hudon, Middletown, CT (US); Sally Carter, Wallingford, CT (US); Charles Trahan, Torrington, CT (US)

(73) Assignee: Covidien LP, Mansfield, MA (US)

( * ) Notice: Subject to any disclaimer, the term of this patent is extended or adjusted under 35 U.S.C. 154(b) by 367 days.

(21) Appl. No.: 12/716,615

(22) Filed: Mar. 3, 2010

(65) Prior Publication Data

US 2010/0249515 A1  Sep. 30, 2010

Related U.S. Application Data

(60) Provisional application No. 61/164,968, filed on Mar. 31, 2009.

(51) Int. Cl.
  *A61B 1/32* (2006.01)
(52) U.S. Cl.
  USPC ........................................................ 600/201
(58) Field of Classification Search
  USPC  600/201, 104, 154, 159; 604/167.01–167.14,
    604/247, 249; 606/107, 108, 185, 184, 167,
    606/213; 251/149.1
  See application file for complete search history.

(56) References Cited

U.S. PATENT DOCUMENTS

| | | | |
|---|---|---|---|
| 4,177,814 A * | 12/1979 | Knepshield et al. | 604/26 |
| 4,755,173 A | 7/1988 | Konopka et al. | |
| 4,834,720 A | 5/1989 | Blinkhorn | |
| 5,000,745 A * | 3/1991 | Guest et al. | 604/256 |
| 5,207,656 A * | 5/1993 | Kranys | 604/256 |
| 5,407,433 A | 4/1995 | Loomas | |
| 5,411,483 A | 5/1995 | Loomas et al. | |
| 5,628,732 A | 5/1997 | Antoon, Jr. et al. | |
| 5,634,908 A | 6/1997 | Loomas | |
| 5,643,227 A * | 7/1997 | Stevens | 604/264 |
| 6,053,861 A | 4/2000 | Grossi | |
| 6,238,373 B1 | 5/2001 | DeLaTorre et al. | |
| 6,258,065 B1 | 7/2001 | Dennis et al. | |
| 6,482,181 B1 * | 11/2002 | Racenet et al. | 604/167.06 |
| 6,648,853 B1 | 11/2003 | McEntee | |
| 6,860,869 B2 | 3/2005 | Dennis | |
| 7,244,244 B2 * | 7/2007 | Racenet et al. | 604/167.06 |
| 7,371,227 B2 | 5/2008 | Zeiner | |

(Continued)

FOREIGN PATENT DOCUMENTS

WO    WO98/53865    12/1998
WO    WO02/087682   11/2002

OTHER PUBLICATIONS

European Search Report for EP 10 25 0636 date of completion is Jul. 23, 2010 (3 pages).
US 7,282,043, 10/2007, Racenet et al. (withdrawn)

*Primary Examiner* — Pedro Philogene

(57) ABSTRACT

A surgical access portal includes a seal housing, a sleeve mountable to the seal housing, and a seal disposed within the seal housing. The seal includes a first layer having an opening for the reception and passage of a surgical instrument, a second continuous layer for providing a fluid tight seal in the seal housing in the presence and/or in the absence of a surgical instrument, and a third layer having an opening for the passage of a surgical instrument therethrough. The first and third layers have a higher density than the second layer for maintaining the second layer in an axially compressed state therebetween.

12 Claims, 2 Drawing Sheets

U.S. PATENT DOCUMENTS

| | | | |
|---|---|---|---|
| 7,988,679 B2 * | 8/2011 | Daly et al. | 604/247 |
| 8,092,431 B2 * | 1/2012 | Lunn et al. | 604/167.04 |
| 2002/0107484 A1 | 8/2002 | Dennis et al. | |
| 2004/0106942 A1 | 6/2004 | Taylor et al. | |
| 2004/0171990 A1 | 9/2004 | Dennis et al. | |
| 2004/0230161 A1 | 11/2004 | Zeiner | |
| 2005/0085774 A1 * | 4/2005 | Streifinger et al. | 604/167.01 |
| 2005/0096695 A1 * | 5/2005 | Olich | 606/213 |
| 2007/0185453 A1 | 8/2007 | Michael et al. | |
| 2008/0265512 A1 * | 10/2008 | Beckman et al. | 277/301 |
| 2008/0312662 A1 | 12/2008 | Hickingbotham | |

\* cited by examiner

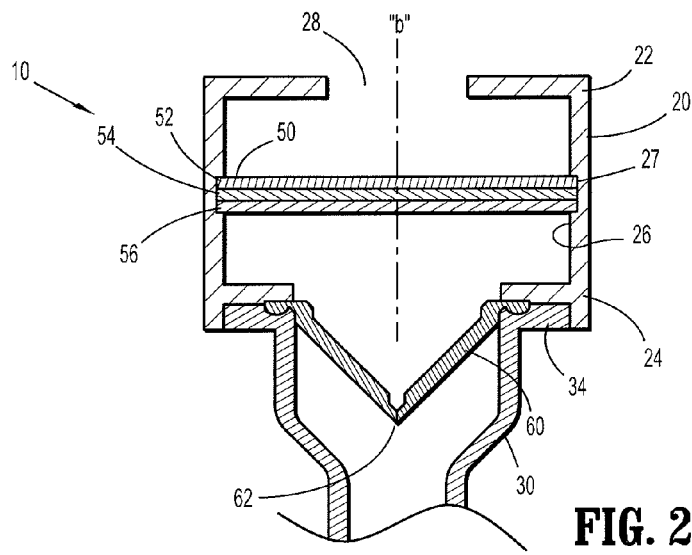
FIG. 2
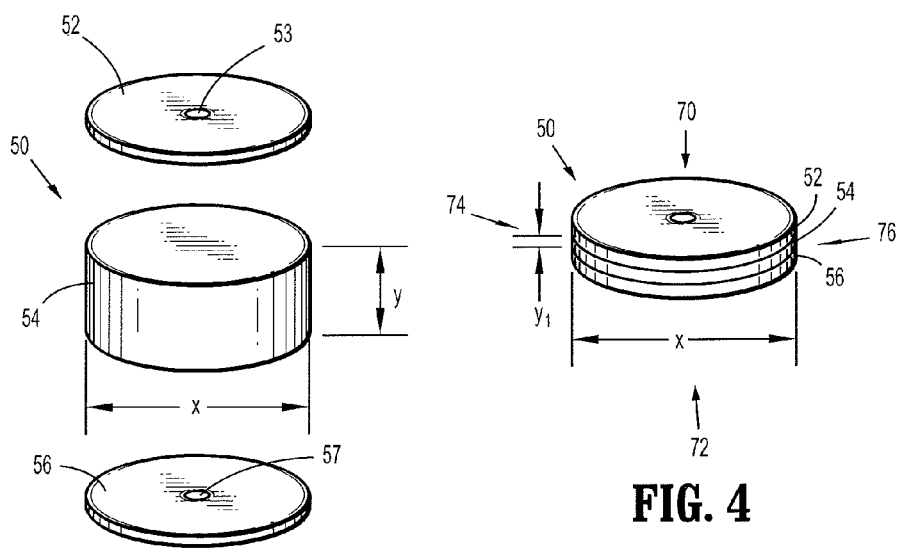
FIG. 3
FIG. 4

ACCESS PORTAL INCLUDING SILICONE FOAM THREE LAYER SEAL

CROSS REFERENCE TO RELATED APPLICATION

The present application claims the benefit of and priority to U.S. Provisional Application Ser. No. 61/164,968 filed on Mar. 31, 2009, the entire contents of which are incorporated herein by reference.

BACKGROUND

1. Field of the Disclosure

The present disclosure relates to surgical devices and, more particularly, relates to a surgical access portal apparatus incorporating a three layer seal for minimizing seal deformation during a minimally invasive surgical procedure.

2. Description of the Related Art

Minimally invasive surgical procedures including endoscopic, arthroscopic, and laparoscopic procedures permit surgery to be performed on organs, tissues, and vessels far removed from an opening within the tissue. These procedures generally require that any instrumentation inserted into the body be sealed, e.g., provisions may be made to ensure that gases and/or liquids do not enter or exit the body through the incision as, for example, in surgical procedures utilizing insufflating or irrigating fluids. These procedures typically employ surgical instruments which are introduced into the body through a cannula. The cannula has a seal associated therewith. The seal is intended to form a substantially fluid tight seal about the instrument to preserve the integrity of the established surgical site.

Seals may be limited by their ability to sustain a seal when a smaller surgical instrument is moved off-axis relative to a central axis of the cannula. Seals may also be limited by their ability to sustain their integrity when the surgical instrument is angulated. Such extreme ranges of motion of smaller diameter surgical instruments within the cannula can create a "cat eye" or crescent shaped gap in the seal that can result in a loss of seal integrity. This difficulty in maintaining seal integrity is increased when sutures are also present alongside of the surgical instrument. Additional problems include the flexibility of the seal in maintaining its integrity when both small diameter and large diameter surgical instruments are used.

SUMMARY

Accordingly, an access portal includes a sleeve and a seal housing having a multi-layer seal. The seal includes at least a first layer having an opening for the reception and passage of a surgical instrument, a second continuous layer for providing a fluid tight seal in the seal housing in the presence and/or in the absence of a surgical instrument, and a third layer having an opening for the passage of a surgical instrument therethrough. The first and third layers have a higher density than the second layer for maintaining the second layer in an axially compressed state therebetween. The second layer may also be radially compressed or constricted by the sidewall, or a channel in the sidewall, of the seal housing.

BRIEF DESCRIPTION OF THE DRAWINGS

Embodiments of the present disclosure will be better appreciated by reference to the drawings wherein:

FIG. 2 is a cross-sectional view of the seal housing and sleeve of the portal apparatus of FIG. 1;

FIG. 3 is a perspective view of a seal of the present disclosure in an unassembled state; and FIG. 4 is a perspective view of the seal of FIG. 3 in an assembled state.

DETAILED DESCRIPTION

Figure 1:
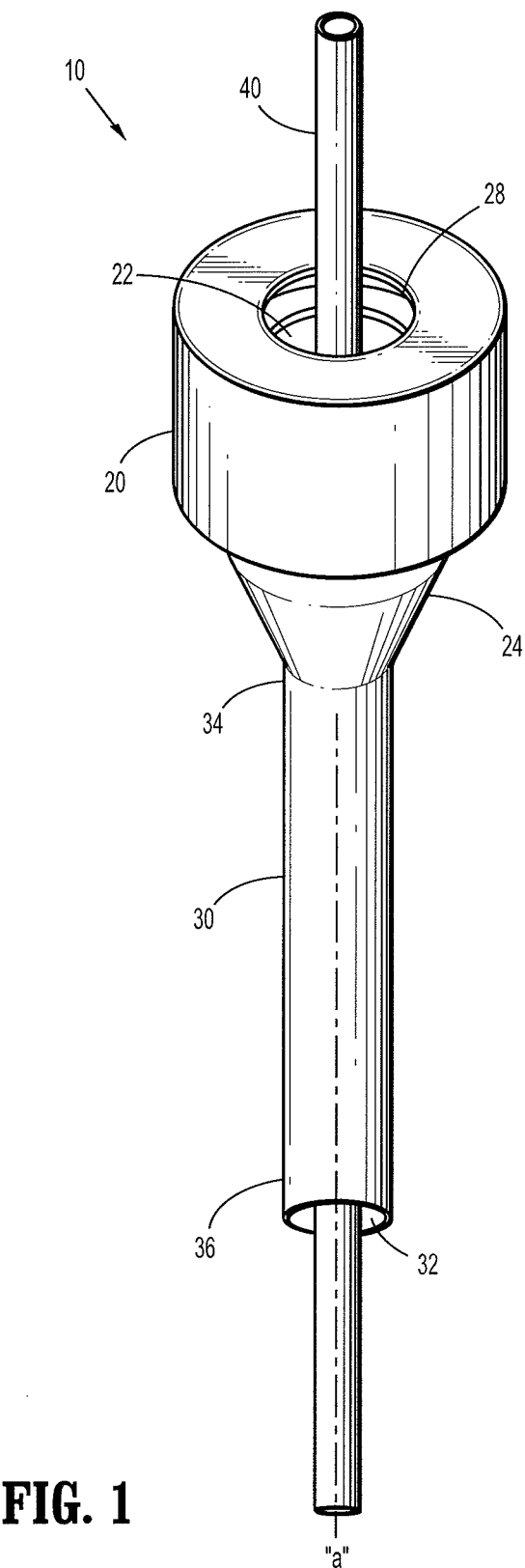
FIG. 1 is a perspective view of a portal apparatus in the form of a seal housing and sleeve in accordance with the principles of the present disclosure.

The portal apparatus of the present disclosure incorporates a seal housing either alone or in combination with a sleeve housing for introduction into a body cavity of a patient. The portal apparatus is adapted for receiving objects therethrough. The seal housing of the portal apparatus incorporates a seal which, either alone or in combination with a valve, provides a substantial seal between a body cavity of a patient and the outside atmosphere before, during, and after insertion of an object through the portal assembly.

The seal contemplates the introduction and manipulation of various types of instrumentation adapted for insertion through a trocar, cannula, or other portal assembly. A fluid tight interface is maintained via the seal about the instrumentation inserted therethrough, as well as in some embodiments in the absence of an instrument, to maintain the interior of the seal housing under seal. This substantially prevents gas and/or liquid leakage from the established surgical site so as to preserve the atmospheric integrity of a surgical procedure.

The seal is capable of accommodating objects of varying diameters, e.g., instruments from about 3 mm to about 18 mm, by providing a fluid tight seal with each objected inserted therethrough. The flexibility of the seal greatly facilitates endoscopic surgery, including laparoscopic and arthroscopic procedures, where a variety of surgical instruments having differing diameters are often needed during a single surgical procedure. Examples of surgical instrumentation which may be introduced through the portal apparatus include clip appliers, graspers, dissectors, retractors, staplers, laser probes, photographic devices, endoscopes, laparoscopes, arthroscopes, tubes, electrosurgical cutting, coagulating and ablation devices, and other tools within the purview of those skilled in the art. Such instruments will be collectively referred to herein as "instruments" or "instrumentation."

Referring now to the drawings, in which like reference numerals identify identical or substantially similar parts throughout the several views, FIG. 1 illustrates a portal apparatus 10 of the present disclosure incorporating seal housing 20 mounted to sleeve 30. In embodiments, the portal apparatus 10 is particularly adapted for use in arthroscopic surgery where irrigating fluids are pumped into the surgical field. In other embodiments, the portal apparatus 10 is particularly adapted for use in laparoscopic surgery where the peritoneal cavity is insufflated with a suitable gas, e.g., $CO_2$, to raise the cavity wall from the internal organs therein. The sleeve 30 is typically used with an obturator assembly (not shown) which may be a blunt, non-bladed, or sharp pointed instrument positionable within the passageway of the sleeve 30. The obturator assembly is utilized to penetrate a body wall or to introduce the sleeve 30 through the body wall, and then subsequently is removed from the sleeve 30 to permit introduction of surgical instrumentation 40 utilized to perform the procedure through the passageway and body wall.

Sleeve 30 may be any portal member, such as a cannula or trocar assembly, suitable for the intended purpose of accessing a body cavity and typically defines an internal longitudinal passageway 32 dimensioned for permitting introduction and passage of instruments 40 therethrough. Sleeve 30 defines a central longitudinal axis "a" extending along the length of sleeve 30 and has proximal (or leading) end 34 and distal (or trailing) end 36. Sleeve 30 may be formed of any suitable medical grade material, such as metal materials like stainless steel, titanium, and aluminum; polymeric materials like acrylonitrile-butadiene-styrene, polycarbonate, and polystyrene; and other rigid materials and combinations thereof as envisioned by one skilled in the art.

Sleeve 30 may be transparent, translucent, or opaque. The diameter of sleeve 30 may vary, but, typically ranges from about 3 mm to about 18 mm. Sleeve 30 may or may not include means for facilitating retention of the sleeve 30 within tissue. Such means may include a plurality of locking elements, ribs, or other locking arrangements within the purview of those skilled in the art.

Mounted adjacent proximal end 34 of sleeve 30 is seal housing 20. Sleeve 30 may be releasably secured or connected to seal housing 20 by conventional means including a bayonet coupling, a threaded connection, a snap fit, a friction fit, a tongue and groove arrangement, cam-lock mechanisms, or any other joining means envisioned by one skilled in the art for detachably mounting seal housing 20 to proximal end 34 of sleeve 30. Alternatively, seal housing 20 may be permanently secured to sleeve 30 by conventions means, such as for example, ultrasonic welding, use of adhesives, or by monolithically forming seal housing 20 with sleeve 30. Sleeve 30 may also incorporate an o-ring seal (not shown) disposed between proximal end 34 of sleeve 30 and seal housing 20 to assist in sealing the interior passages of portal apparatus 10.

With reference to FIG. 2, in conjunction with FIG. 1, seal housing 20 houses the sealing components, or seal assembly, of the apparatus. Seal housing 20 defines central seal housing axis "b" which may be parallel to the axis "a" of sleeve 30 and, more specifically, coincident with axis "a" of the sleeve 30 when seal housing 20 is mounted to sleeve 30. Seal housing 20 may be integrally or monolithically formed as a single unit or may incorporate multiple components connected to each other through any of the aforementioned connection means, which, when assembled together, form seal housing 20. Seal housing 20 may be composed of the same or similar materials as sleeve 30 described above.

Seal housing 20 includes proximal end 22, distal end 24, and sidewall 26 disposed therebetween. Proximal end 22 defines central aperture 28 for receiving the surgical instrument. The central aperture 28 may be of a sufficient diameter to permit passage of relatively large sized instruments. Distal end 24 of seal housing 20 includes a complementary joining member to the proximal end 34 of sleeve 30 for joining the two components as discussed above. Distal end 24 may also be adapted to accommodate valve 60 as will be discussed. Sidewall 26 may define an internal peripheral channel or recess 27 for receiving a portion or component of seal 50. Internal peripheral channel or recess 27 may be defined along any portion of sidewall 26, in embodiments recess 27 is disposed approximately adjacent the longitudinal midpoint of the seal housing 20.

Optional valve 60 is placed distal, or internal to, seal 50. Valve 60 may be a zero-closure valve such as a duck-bill valve having slit 62 which is adapted to close in the absence of a surgical instrument and/or in response to insufflation gases of the pressurized cavity. Further, valve 60 prevents fluids or debris from entering seal housing 20 when the valve 60 is closed. Fluid pressure on valve 60 will close slit 62 thereby sealing seal housing 20 from fluids. When an instrument is inserted through valve 60, however, a seal is not always formed around the instrument thereby allowing some fluid to enter seal housing 20 wherein seal 50 prevent the fluid from exiting seal housing 20. In the alternative, valve 60 may be a gel seal, balloon valve, or a flapper valve.

Seal 50 is generally disc-shaped and sized to fit within seal housing 20. Seal 50 is configured to form a fluid-tight fit about surgical instrument 40. As illustrated in the current embodiment, seal 50 is flat or planar. It is envisioned that seal 50 may be any shape, such as having a tapered or funneled profile, for sealing and maintaining the integrity of the established surgical site.

Seal 50 is a multi-layered seal having at least three layers, including an inner layer sandwiched between two outer layers as illustrated in FIGS. 3 and 4. Seal 50 includes, from proximal to distal end, first (or outer) layer 52, second (or inner) layer 54, and third (or outer) layer 56. It is envisioned that seal 50 may also be composed of additional layers including fabrics, elastomers, foams, gels, combinations thereof, or combinations with other materials to form a layered composite.

First layer 52 and third layer 56 may each be in the form of disc-shaped layers. First and third layers 52, 56 generally enhance the structural integrity and durability of the seal 50 by providing a support lattice or structure to encapsulate, support, and compress second layer 54. Accordingly, the first and third layers 52, 56 have a higher density than second layer 54 in order to create the axial resistance needed to maintain reasonable compressive forces in the second layer 54 during insertion and withdrawal of the surgical instrument therethrough. First and third layers 52, 56 may also reduce instrument insertion forces and provide protection to the second layer 54 thereby minimizing the potential of puncture with the surgical instrument during insertion. In embodiments, the first and/or third layers 52, 56 may be formed from a protective fabric or a penetration resistant elastomer. First and third layers 52, 56 may be fabricated from the same, or different, materials and may be of the same, or varying, weight, size, and thickness.

In embodiments, first layer 52 and/or third layer 56 may comprise a woven, knitted, braided, or non-woven fabric of natural or synthetic materials. In embodiments, the fabric may be densely or tightly configured and/or include more than one layer to form a composite of fabrics. Suitable yarns and fabric materials include synthetic materials such as SPANDEX™ containing LYCRA™ which is commercially available from Milliken of South Carolina, nylon, Kevlar™ manufactured by E.I. DuPont de Nemours and Company, and other materials that will expand and compress about an instrument inserted therethrough, while providing rigidity and support to the seal 50, are envisioned.

In other embodiments, first layer 52 and/or third layer 56 may be fabricated from elastomers or thermoplastic polymers. Suitable elastomeric materials include polyisoprene, polychloroprene, polyester, polyurethane, polyether urethane, polyvinyl chloride, ethylene vinyl acetate, polybutadiene, polyether block amide, styrene block copolymer, ethylene propylene diene M-class rubber, nitrile rubber, butyl rubber, natural rubber, silicone, and copolymers and combinations thereof.

First and third layers 52, 56 may each define an aperture or opening 53, 57 respectively, to permit passage of a surgical instrument therethrough. As illustrated in the current embodiments, circular openings may be defined about central seal axis "b." It is also envisioned that single or multiple intersecting slits may be formed within first and/or third layers 52, 56. In embodiments, the slit(s) may be substantially linear and extend outwardly from seal axis "b." Other arrangements, such as non-linear slit, or randomly spaced, equidistally spaced, and/or radially spaced slits, are also contemplated. Slits may assist in reducing insertion forces needed to advance the surgical instrument into the surgical site by reducing radial constriction of the inner areas of the first and third layers 52, 56 about the instrument. In embodiments, the first and/or third layer 52, 56 may be coated to inhibit penetrability other than through the predefined aperture, such as with an epoxy. Alternatively, one or both of first and third layers 52, 56 may be constructed as continuous layers of penetrable, yet structurally supportive material.

Second layer 54 may be fabricated from an open or closed cell foam material which forms a seal about a surgical instrument inserted therethrough. Foam materials may have sufficient elasticity to bend and deform about an inserted instrument while conforming to the outer dimensioning of the instrument thereby establishing a fluid tight seal about the object. Foam materials may also be sufficiently compliant to absorb off axis motion of the instrument. Moreover, the compliant characteristics of a foam may substantially minimize the formation of a gap around the instrument during off-set manipulation of the instrument. In addition, the second layer 54 is well suited for applications in which one or more sutures are also present, along with the surgical instrument 40. While the presence of sutures alongside the surgical instrument 40 may result in an irregular sealing surface that typically makes it more difficult to maintain a seal, the elasticity of the second layer 54 of the present invention helps to improve the sealing characteristics by minimize the formation of such gaps even when sutures are present and cause an irregular sealing surface. The presence of a gap would otherwise permit the undesired release of gases from the insufflated body cavities, such as a pneumoperitoneum, or the release of liquids during irrigation of a body cavity, such as a knee joint.

In embodiments, the second layer 54 is a foam composed of elastomeric or thermoplastic materials as described above. The second layer 54, however, has a lower density than the first and third layers 52, 56 in order to impart the desired sealing characteristics. The second layer 54 may be soft enough to be penetrated by a surgical instrument under manual pressure. The second layer 54 may be self-healing so that it does not visibly tear or scar when the surgical instrument is removed. And the second layer 54 may be resilient and have a sufficiently high elasticity so that it does not permanently deform during use.

Referring to FIG. 3, second layer 54, in a natural or unstressed state, includes a diameter "x" and a height "y." Upon assembly with the first and third layers 52, 56 the second layer 54 is axially compressed as shown in the direction of arrows 70 and 72 of FIG. 4 to a compressed or stressed height "$y_1$" which is less than the unstressed height "y." Second layer 54 may also be axially compressed as shown in the direction of arrows 74 and 76 so that the diameter of the seal 50 remains about "x."

The second layer 54 may be maintained under axial compression by first and third layers 52, 56 within seal housing 20, even when no surgical instrument is placed therethrough. The second layer 54 may also be under radial compression or at least restricted by sidewall 26, or channel 27 of sidewall 26, of seal housing 20. The diameter of the sidewall 26 may be a smaller diameter so that seal 50 is compressed therein or the sidewall 26 may be the same diameter as the seal 50 to form a snug fit therewith and restrict radial expansion of the seal 50. Accordingly, an axially passing surgical instrument increases the radial force of the second layer 54 until the instrument is removed and the compressive forces placed on the second layer 54 effectively close any gaps formed by the instrument.

In embodiments, second layer 54 may have a small diameter orifice or slit which is closed upon radial and axial compression of seal 50 thereby providing a tight seal 50 in both the presence and the absence of a surgical instrument. The orifice or slit effectively lowers the insertion pressure needed to insert a surgical instrument therethrough and minimizes potential cutting or tearing of the second layer 54 by the instrument.

First, second, and third layers 52, 54, 56 of seal 50 may either individually or collectively incorporate a lubricant, a therapeutic or pharmacological agent, or combinations thereof. Lubricants are within the purview of those skilled in the art for having a smoothness or slipperiness such that it makes a surface relatively free from friction. Examples of therapeutic or pharmacological agents include antimicrobials, antibacterials, hemostatic, moisture-providing agents, such as saline, healing agents, lubricious agents, analgesics, antiseptics, and/or anti-inflammatory agents.

Seal 50 may be formed by various methods. In one exemplary method, a raw, i.e., uncured foam inner layer 54 is positioned between two outer layers 52, 56 of resilient material. The layers 52, 54, 56 are placed into a hot compression mold substantially the same shape and size as the finished seal 50 to cure the foam. The outer layers 52, 56 are compressed into the inner layer 54 while axially compressing the seal 50. The foam also expands outwardly during curing and the outer portions are radially compressed by the mold. In another exemplary method of forming the seal 50, outer layers 52, 56 are stretched and held under tension while they are bonded to opposite surfaces of inner layer 54 via techniques within the purview of those skilled in the art. Inner layer 54 may be a foam in an uncured state which, upon curing is maintained in a compressed state by the radial tension of the outer layers 52, 56. Alternatively, the inner layer 54 may be a cured foam subject to a compressive force, with or without the addition of heat or chemical additives, which remains in a compressed state by the radial tensions of the outer layers 52, 56. Layers 52, 56 may be provided with apertures 53, 57 prior to assembly via any of the aforementioned methodologies.

To use portal apparatus 10 in connection with the performance of a surgical task during a surgical procedure, seal housing 20 is mounted to sleeve 30 as discussed above. The assembled portal apparatus 10 is introduced into a body cavity typically utilizing a sharp or non-blade trocar obturator to access the cavity and the obturator is removed. A surgical instrument 40 may be advanced through portal apparatus 10 by inserting the instrument into aperture 28 of seal housing 20 and through seal 50 whereby the portions defining aperture 53 of the first layer 52 of the seal 50 stretch to accommodate the instrument in substantial sealed relation therewith while being rigid enough to maintain axial compression of the seal 50 such that there is little reaction force in the axial direction during insertion of the surgical instrument 40. Second layer 54 of the seal 50 accommodates and conforms to the passing instrument 40 creating a seal thereabout with a radial reaction force to prevent formation of any gaps on opposed sides of the instrument 40 and any sutures present. Third layer 56 provides for similar passage of surgical instrument 40 as first layer 52. The instrument 40 is then distally passed through optional valve 60, into sleeve 30, and into the body cavity. The desired surgical task is performed with the instrument 40. Upon withdrawal of the surgical instrument 40, the radial pressure exerted on the inner layer 54 is eliminated thereby forcing the hole formed by the instrument 40 to close or become smaller. In an embodiment, a self-healing nature of the seal 50 may help maintain a seal within the seal housing 20 in both the presence and the absence of a surgical instrument.

It will be understood that various modifications and changes in form and detail may be made to the embodiments of the present disclosure without departing from the spirit and scope of the disclosure. Therefore, the above description should not be construed as limiting the disclosure but merely as exemplifications of the embodiments thereof. Those skilled in the art will envision other modifications within the scope and spirit of the present disclosure as defined by the claims appended hereto.

What is claimed is:

1. An access portal comprising:
    a seal housing;
    a sleeve mountable to the seal housing, the sleeve having an internal longitudinal passage adapted to provide access to underlying tissue; and
    a seal disposed within the seal housing, the seal comprising:
        a first layer having an opening for reception and passage of a surgical instrument;
        a second continuous uninterrupted layer of a penetrable material for providing a fluid tight seal in the seal housing in the presence of a surgical instrument; and
        a third layer having an opening for the passage of the surgical instrument therethrough,
        the first and third layers having a higher density than the second layer for maintaining the second layer in an axially compressed state between the first and third layers.

2. The access portal according to claim 1, wherein the seal housing further includes a valve distally spaced from the seal.

3. The access portal according to claim 1, wherein the seal is radially compressed via a channel in the seal housing.

4. The access portal according to claim 1, wherein the diameter of the seal is radially constricted by a channel in the seal housing.

5. The access portal according to claim 1, wherein the first and third layers of the seal are selected from the group consisting of fabric layers, elastomeric layers, thermoplastic layers, and combinations thereof.

6. The access portal according to claim 1, wherein the second layer is a foam.

7. The access portal according to claim 6, wherein the second layer is a silicone foam.

8. The access portal according to claim 1, wherein the second continuous layer also provides a fluid tight seal in the seal housing in the absence of a surgical instrument.

9. The access portal according to claim 1, wherein the seal housing is an integral structure including a proximal end including a proximal wall defining an aperture, a distal end including a distal wall defining an aperture, and a sidewall disposed therebetween including an internal peripheral channel, the seal being disposed between the proximal and distal ends, and a portion of the seal being positioned within the internal peripheral channel of the sidewall.

10. An access portal comprising:
    a sleeve having an internal longitudinal passage adapted to provide access to underlying tissue; and
    a seal housing mountable to the sleeve, the seal housing having a proximal end defining an aperture for receiving a surgical instrument and including a seal disposed entirely within the seal housing, the seal comprising:
        a first layer having an opening for reception and passage of a surgical instrument;
        a second continuous layer for providing a fluid tight seal in the seal housing in the presence and in the absence of a surgical instrument; and
        a third layer having an opening for the passage of a surgical instrument therethrough.

11. The access portal according to claim 10, wherein the second continuous layer is axially compressed between the first and third layers.

12. The access portal according to claim 10, wherein the seal housing is an integral structure with the proximal end including a proximal wall defining the aperture, a distal end including a distal wall defining an aperture for passage of the surgical instrument therethrough, and a sidewall disposed between the proximal and distal ends, the sidewall including an internal peripheral channel wherein a portion of the seal is positioned within the internal peripheral channel of the sidewall.

\* \* \* \* \*